US009944688B2

(12) United States Patent
Lim et al.

(10) Patent No.: US 9,944,688 B2
(45) Date of Patent: Apr. 17, 2018

(54) NON-PEPTIDYL POLYMER-INSULIN MULTIMER AND METHOD FOR PRODUCING THE SAME

(75) Inventors: Sung In Lim, Hwaseong-si (KR); Myung Hyun Jang, Seoul (KR); Dae Jin Kim, Hwaseong-si (KR); Sung Youb Jung, Suwon-si (KR); Se Chang Kwon, Seoul (KR)

(73) Assignee: HANMI SCIENCE CO., LTD., Hwaseong-si (KR)

( * ) Notice: Subject to any disclaimer, the term of this patent is extended or adjusted under 35 U.S.C. 154(b) by 186 days.

(21) Appl. No.: 14/123,258

(22) PCT Filed: Jun. 1, 2012

(86) PCT No.: PCT/KR2012/004368
§ 371 (c)(1),
(2), (4) Date: Dec. 2, 2013

(87) PCT Pub. No.: WO2012/165916
PCT Pub. Date: Dec. 6, 2012

(65) Prior Publication Data
US 2014/0107023 A1 Apr. 17, 2014

(30) Foreign Application Priority Data
Jun. 2, 2011 (KR) .................. 10-2011-0053487

(51) Int. Cl.
*A61K 47/48* (2006.01)
*A61K 38/28* (2006.01)
*A61K 47/30* (2006.01)
*A61P 3/10* (2006.01)
*C07K 14/62* (2006.01)
*A61K 47/60* (2017.01)
*A61K 47/52* (2017.01)
*A61K 47/69* (2017.01)

(52) U.S. Cl.
CPC .............. *C07K 14/62* (2013.01); *A61K 38/28* (2013.01); *A61K 47/52* (2017.08); *A61K 47/60* (2017.08); *A61K 47/6921* (2017.08)

(58) Field of Classification Search
None
See application file for complete search history.

(56) References Cited

U.S. PATENT DOCUMENTS

| 5,672,662 A * | 9/1997 | Harris .................. C08G 65/329 525/326.8 |
| 2005/0266465 A1 | 12/2005 | Patten et al. |
| 2009/0004118 A1 | 1/2009 | Nie et al. |
| 2009/0312236 A1 * | 12/2009 | Beals et al. ........................ 514/3 |
| 2011/0105392 A1 | 5/2011 | Beals et al. |
| 2011/0165647 A1 | 7/2011 | Fernig et al. |

FOREIGN PATENT DOCUMENTS

| CN | 102065884 A | 5/2011 |
| TW | 200611910 A | 4/2006 |
| TW | 201010728 A1 | 3/2010 |
| WO | 2009/098510 A2 | 8/2009 |
| WO | 2009152128 A1 | 12/2009 |

OTHER PUBLICATIONS eMedicine Health, diabetes causes, http://www.onhealth.com/diabetes_health/page3.htm#diabetes_causes (referenced Aug. 22, 2013).*
United Health Care; Diabetes, available at http://www.uhc.com/source4women/health_topics/diabetes/relatedinformation/d0f0417b073bf110VgnVCM1000002f10b10a_.htm (referenced Aug. 22, 2013).*
Lim et al., "Cobalt(III)-induced hexamerization of PEGylated insulin," Int. J. Biol. Macromol. 49:832-837 (online Aug. 3, 2011).*
Kurtzhals et al., "The Cobalt(III)-Insulin Hexamer is a Prolonged-Acting Insulin Prodrug," J. Pharm. Sci. 84:1164-1168 (1995).*
Hinds et al., "Effects of PEG conjugation on insulin properties," Adv. Drug. Del. Rev. 54:505-530 (2002).*
Storm et al., "The Glu( B13) Carboxylates of the Insulin Hexamer Form a Cage for Cd2+ and Ca2+ Ions," Biochem. 24:1749-1756 (1985).*
Dou et al., "Synthesis and Purification of Mono-PEGylated Insulin," Chem Biol Drug Des 69:132-138 (2007).*
Takashi Uchio et al. Site-specific insulin conjugates with enhanced stability and extended action profile. Advanced Drug Delivery Reviews. 1999, pp. 289-306. vol. 35.
Boris N. Novikov et al. Improved pharmacokinetics and immunogenicity profile of organophosphorus hydrolase by chemical modification with polyethylene glycol. Journal of Controlled Release. 2010, pp. 318-325. vol. 146 ,Issue 3.
Havelund et al. The Mechanism of Protraction of Insulin Detemir, a Long-acting, Acylated Analog of Human Insulin, Pharmaceutical Research, 2004, pp. 1498-1504, vol. 21, No. 8.
Hinds et al., Synthesis and Characterization of Poly(ethylene glycol)-Insulin Conjugates, Bioconjugate Chem., 2000, pp. 195-201, 11.
Taiwan Patent Office, Communication dated Apr. 7, 2014, issued in corresponding Taiwanese application No. 101119710.
Peter Kurtzhals et al; "The Cobalt(III)-Insulin Hexamer is a Prolonged-Acting Insulin Prodrug"; Journal of Pharmaceutical Sciences vol. 84, No. 10, Oct. 1995; pp. 1164-1168; American Chemical Society and American Pharmaceutical Association.
Sung In Lim et al; "Cobalt(III)-induced hexamerization of PEGylated insulin"; International Journal of Biological Macromolecules 49 (2011) pp. 832-837.
Japanese Patent Office, Communication dated Feb. 23, 2016 issued in counterpart application No. 2014-513451.

(Continued)

*Primary Examiner* — Julie Ha
*Assistant Examiner* — Kristina M Hellman
(74) *Attorney, Agent, or Firm* — Sughrue Mion, PLLC (57) ABSTRACT

The present invention relates to a non-peptidyl polymer-insulin multimer comprising two or more of a non-peptidyl polymer-insulin conjugate prepared by linking a non-peptidyl polymer and insulin via a covalent bond, in which the conjugates are complexed with cobalt ion to form a multimer, a method and kit for the preparation of the multimer, a pharmaceutical composition for the prevention or treatment of diabetes comprising the multimer as an active ingredient, and a method for preventing or treating diabetes by administering the composition to a subject.

16 Claims, 3 Drawing Sheets

(56) References Cited

OTHER PUBLICATIONS

Jorgen F. Hansen; "The self-association of zinc-free human insulin and insulin analogue B13-glutamine"; Biophysical Chemistry vol. 39, 1991; pp. 107-110.
Starkova N.T.// Klinicheskaya endocrinologiya. Rukovodstvo. 3 izd., pererab. i dop. // Spb.: Piter, 2002, pp. 263-270 (11 pgs. total).
Russian Patent Office, Communication dated May 20, 2016, issued in counterpart Russian application No. 2013152687/10.
Chinese Patent Office (SIPO), Office Action dated Jan. 30, 2015, issued in corresponding Chinese application No. 201280038302.7, with English translation.

\* cited by examiner

NON-PEPTIDYL POLYMER-INSULIN MULTIMER AND METHOD FOR PRODUCING THE SAME

CROSS REFERENCE TO RELATED APPLICATIONS

This application is a National Stage of International Application No. PCT/KR2012/004368 filed Jun. 1, 2012, claiming priority based on Korean Patent Application No. 10-2011-0053487 filed Jun. 2, 2011, the contents of all of which are incorporated herein by reference in their entirety.

TECHNICAL FIELD

The present invention relates to a non-peptidyl polymer-insulin multimer comprising two or more of a non-peptidyl polymer-insulin conjugate prepared by linking a non-peptidyl polymer and insulin via a covalent bond, in which the conjugates are complexed with cobalt ion to form a multimer, a method and kit for the preparation of the multimer, a pharmaceutical composition for the prevention or treatment of diabetes comprising the multimer as an active ingredient, and a method for preventing or treating diabetes by administering the composition to a subject.

BACKGROUND ART

Insulin is composed of 51 amino acids, and has a molecular weight of 5808 dalton (Da). Insulin is produced in the beta cells of islets of Langerhans in the pancreas, and is stored as a hexamer (a unit of six insulin molecules) before being absorbed into the blood vessel in a biologically active monomeric form. The hexamer formation is facilitated by the coordination of zinc ions and hydrophobic interaction between three dimers. Within the hexamer, two metal ion-binding sites exist and three histidine residues derived from the three dimers are involved in each site. The binding sites exist at both ends of the hexamer or at the bottom of tunnel structure through the center from the surface according to the structural state of the insulin hexamer (T or R state).

Currently, most commercial recombinant insulin and insulin analogues exist as hexamer formulations. That is, they are formulated by including 3 mg/mL or more of insulin in a buffer solution containing the hexamer-stabilizing compounds, zinc and phenol (or cresol). Compared to the monomeric forms, the hexamer formulations provide excellent resistance to fibrillation and deamination, thereby improving the stability of insulin and extending the expiration date. Moreover, after subcutaneous injection, the hexamer formulations show a slower absorption from the injection site into the blood than the monomeric form, and thus they have the advantage of sustained duration of action. According to the previous studies, the slow absorption rate is explained by an inverse relation between the molecular size and capillary permeability at the depot. These properties of hexamers were applied to the recently developed long-acting insulin analogues to cause a delayed or sustained absorption of insulin after subcutaneous injection. A representative example is an insulin detemir prepared by the attachment of a fatty acid chain to a lysine at position 29 on the B chain of native insulin (Havelund et al., 2004). According to this study, while insulin detemir injected forms in the body a dihexamer, it forms a large molecular complex by hydrophobic interaction with albumin. Thus, subcutaneous half-life, which is a time taken by half of the drug injected subcutaneously to pass through the capillary wall, was 4 times longer than the native insulin hexamer.

However, the hexamer formulations are disadvantageous in that they cannot be applied to insulin analogues that have modification at the first amino acid phenylalanine on the B chain of native insulin, because the phenylalanine residue is involved in the structural stability of hexamer. According to the previous study using PEGylated insulin (Hinds, et al., 2000), when insulin analogues prepared by attachment of 750 Da or 2,000 Da-sized PEG to the amino terminus of the B chain of native insulin were analyzed by UV-circular dichroism and sedimentation equilibrium, most of them existed as a monomer within the concentration range of 0.1-1.0 mM. On the contrary, native insulin mostly exists as a hexamer within the corresponding concentration range. Thus, it is difficult to have the advantage of sustained absorption of insulin after subcutaneous injection using the formulated PEGylated insulin hexamer. Other examples of the insulin analogues are albumin-insulin conjugate, glycosylated insulin or the like.

Therefore, there is a urgent need to develop a formulation that induces multimer formation of insulin analogues for the improvement of their pharmacological properties such as stability and sustainability.

DISCLOSURE

Technical Problem

Accordingly, the present inventors induced formation of PEG-insulin hexamers using cobalt ions, and then analyzed their pharmacological properties. As a result, it was found that dissociation of PEG-insulin hexamers into monomers occurred according to a gradual concentration change from micromole (µM) to nanomole (nM), its hydrodynamic volume was greatly increased compared to PEG-insulin conjugates and insulin hexamer, and the PEG-insulin hexamer maintained the stable hexamer form compared to the commercial long-acting insulin, thereby completing the present invention.

Technical Solution

An object of the present invention is to provide a non-peptidyl polymer-insulin multimer comprising two or more of a non-peptidyl polymer-insulin conjugate prepared by linking a non-peptidyl polymer and insulin via a covalent bond, wherein the conjugates are complexed with cobalt ion to form a multimer.

Another object of the present invention is to provide a preparation method of the non-peptidyl polymer-insulin multimer, comprising the step of reacting the non-peptidyl polymer-insulin conjugates with a solution containing cobalt ions to produce non-peptidyl polymer-insulin multimers.

Still another object of the present invention is to provide a pharmaceutical composition for the prevention or treatment of diabetes, comprising the non-peptidyl polymer-insulin multimer as an active ingredient.

Still another object of the present invention is to provide a method for preventing or treating diabetes, comprising the step of administering the pharmaceutical composition to a subject having diabetes or suspected of having diabetes.

Still another object of the present invention is to provide a kit for the preparation of the non-peptidyl polymer-insulin multimer, comprising non-peptidyl polymer-insulin conjugates prepared by linking a non-peptidyl polymer and insulin via a covalent bond; and a solution containing cobalt ions, wherein the solution contains a salt that dissociates into divalent cobalt ions by solvation in an aqueous solution and an oxidant, a hydrate of the salt that dissociates into divalent cobalt ions by solvation in an aqueous solution and an oxidant, or a salt that dissociates into trivalent cobalt ions by solvation in an aqueous solution or a hydrate thereof.

Advantageous Effects

The non-peptidyl polymer-insulin multimer of the present invention is advantageous in that it has a remarkably large hydrodynamic volume and high stability compared to a non-peptidyl polymer-insulin conjugate and a insulin multimer. Therefore, after subcutaneous injection, the multimer of the present invention has a large volume before dissociation into monomers by natural dilution, and thus its rapid absorption into the bloodstream does not occur. Accordingly, a large amount of the drug can be given at once. In addition, since it has a property of slow dissociation into monomers, it is useful in the development of long-acting insulin formulations.

BEST MODE

In one aspect, the present invention provides a non-peptidyl polymer-insulin multimer comprising two or more of a non-peptidyl polymer-insulin conjugate that is prepared by linking a non-peptidyl polymer and insulin via a covalent bond, wherein the conjugates are complexed with cobalt ion to form a multimer.

As used herein, the term "non-peptidyl polymer-insulin conjugate" refers to a conjugate in which non-peptidyl polymer and insulin is linked via a covalent bond. In the present invention, the non-peptidyl polymer-insulin conjugate functions as a monomer which constitutes the non-peptidyl polymer-insulin multimer.

Preferably, the non-peptidyl polymer-insulin conjugate may be a conjugate prepared by linking non-peptidyl polymer to the amino terminus of the A chain of insulin, the amino terminus of the B chain of insulin, or a lysine at position 29 of the B chain of insulin via a covalent bond, and more preferably, is a conjugate prepared by linking non-peptidyl polymer to the amino terminus of the B chain of insulin via a covalent bond.

As used herein, the term "insulin" refers to a peptide that is secreted by the pancreas in response to elevated glucose levels in the blood to take up glucose in the liver, muscle, or adipose tissue and turn it into glycogen, and to stop the use of fat as an energy source, and thus control the blood glucose level. This peptide includes native insulin, native insulin agonists, native insulin precursors, insulin derivatives, fragments thereof, and variants thereof.

The term, "Native insulin" is a hormone that is secreted by the pancreas to promote glucose absorption and inhibit fat breakdown, and thus functions to control the blood glucose level. Insulin is formed from a precursor which is not involved in regulating the blood glucose level, known as proinsulin, through processing. The amino acid sequences of insulin are as follows:

```
Alpha chain:
                                               (SEQ ID NO. 1)
Gly-Ile-Val-Glu-Gln-Cys-Cys-Thr-Ser-Ile-Cys-Ser- Leu-Tyr-Gln-Leu-Glu-Asn-Tyr-Cys-Asn Beta chain:
                                               (SEQ ID NO. 2)
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Pro-Lys-Thr
```

The native insulin is a heterodimer formed by linking the A chain and the B chain via two inter-disulfide bonds, in which a cysteine at position 6 of the A chain and a cysteine at position 7 of the B chain, and a cysteine at position 20 of the A chain and a cysteine at position 19 of the B chain form disulfide bonds, respectively.

The term "insulin agonist" means a compound that binds to the insulin receptor to show biological activity equal to that of insulin, which is irrelevant to the structure of insulin.

The term "insulin variant" is a peptide having one or more amino acid sequences different from those of native insulin, and means a peptide that retains the function of controlling the blood glucose level in the body. The insulin variant may be prepared by any one of substitution, addition, deletion, and modification or by a combination thereof in a part of the amino acid sequences of the native insulin.

The term "insulin derivative" means a peptide having at least 80% amino acid sequence homology with the native insulin, which may have some groups on the amino acid residue chemically substituted (e.g., alpha-methylation, alpha-hydroxylation), deleted (e.g., deamination), or modified (e.g., N-methylation), and has a function of regulating the blood glucose level in the body.

The term "insulin fragment" means a fragment having one or more amino acids added or deleted at the N-terminus or the C-terminus of the native insulin, in which non-naturally occurring amino acids (for example, D-type amino acid) can be added, and has a function of regulating the blood glucose level in the body.

The term "non-peptidyl polymer", as used herein, refers to a biocompatible polymer including two or more repeating units linked to each other by any covalent bond excluding a peptide bond. The non-peptidyl polymer may have a molecular weight of 1 to 100 kDa, and preferably of 1 to 20 kDa.

In addition, the non-peptidyl polymer may have a single terminal reactive group or double terminal reactive group capable of binding with a protein. Preferably, the reactive group may be selected from the group consisting of aldehyde, propion aldehyde, butyl aldehyde, maleimide and succinimide derivative. In particular, when the non-peptidyl polymer has a reactive aldehyde group at both ends thereof, it is effective in linking at both ends with a insulin and an immunoglobulin with minimal non-specific reactions. A final product generated by reductive alkylation by an aldehyde bond is much more stable than that linked by an amide bond. The aldehyde reactive group selectively binds to an N-terminus at a low pH, and binds to a lysine residue to form a covalent bond at a high pH, such as pH 9.0.

Preferably, the non-peptidyl polymer useful in the present invention may be selected from the group consisting of a biodegradable polymer, a lipid polymer, chitin, hyaluronic acid, and a combination thereof, and more preferably, the biodegradable polymer may be polyethylene glycol, polypropylene glycol, ethylene glycol-propylene glycol copolymer, polyoxyethylated polyol, polyvinyl alcohol, polysaccharide, dextran, polyvinyl ethyl ether, polylactic acid (PLA) or polylactic-glycolic acid (PLGA), and much more preferably, polyethylene glycol (PEG). In addition, derivatives thereof known in the art and derivatives easily prepared by the method known in the art may be included in the scope of the present invention. For example, when L-gamma-glutamate-attached non-peptidyl polymer is used, formation of polymeric insulin multimer may favorably occur due to the interaction between L-gamma-glutamates.

As used herein, the term "non-peptidyl polymer-insulin multimer" or "cobalt non-peptidyl polymer-insulin multimer" is a multimer, in which the non-peptidyl polymer-insulin conjugates are complexed with cobalt ions, and includes a compound that is formed by coordination of cobalt ions to one molecule of the non-peptidyl polymer-insulin multimer.

Preferably, the non-peptidyl polymer-insulin multimer may be a dimer, trimer, tetramer, pentamer or hexamer, and preferably is a non-peptidyl polymer-insulin hexamer.

Preferably, the non-peptidyl polymer-insulin multimer may be a multimer formed by trivalent cobalt cations. The non-peptidyl polymer-insulin multimer formulation for the non-peptidyl polymer-insulin conjugates are formed by using trivalent covalt cation (Co(III)) as a coordinating metal ion. More preferably, the conjugates are complexed with trivalent covalt cation to form the non-peptidyl polymer-insulin hexamer, wherein the trivalent covalt cation forms an octahedral coordination of B10His (Histidines at position 10 of the insulin B chain).

In the specific embodiment of the present invention, one of the non-peptidyl polymer-insulin multimers, non-peptidyl polymer-insulin hexamer includes a compound that is formed by coordination of two or more trivalent cobalt ions to one molecule of the insulin multimer. The cylindrical insulin hexamer having a doughnut shaped cross section is formed by a coordinate bond of divalent zinc ions and a hydrophobic interaction between three insulin dimers in nature. In one insulin hexamer, two metal ion-binding sites exist, and three histidine residues (at position 10 of the B chain) derived from three dimers are involved in each of them. Two trivalent cobalt ions in the metal ion binding sites of the non-peptidyl polymer insulin hexamer stabilize the structure of the hexamer.

The non-peptidyl polymer-insulin multimer of the present invention has a larger hydrodynamic volume than the non-peptidyl polymer-insulin conjugate and cobalt insulin multimer, and has a property of slow dissociation into monomers. Thus, it shows excellent in-vivo duration of efficacy and stability, thereby being useful for the treatment of diabetes.

In one example of the present invention, a mono-PEGylated non-peptidyl polymer-insulin conjugate was prepared by attachment of PEG to the amino terminus of the B chain of insulin (Examples 1 and 2), and in vitro activity of the conjugate was confirmed (Example 3).

Further, when a hexamer (cobalt PEG-insulin hexamer) was prepared using the conjugate and cobalt ions, its hydrodynamic volume was greatly increased (Examples 4 and 5). The cobalt PEG-insulin hexamer showed a 70% or higher hexamer ratio at a low concentration of 0.04 µM, whereas the cobalt insulin hexamer showed a 20% hexamer ratio at the low concentration. Thus, the cobalt PEG-insulin hexamer is stable, because it can be prepared into a hexamer formulation at a low concentration (Example 6). In addition, the cobalt PEG-insulin hexamer shows shorter elution time and lower dissociation coefficient than commercially available long-acting insulin such as Levemir composed of insulin detemir and Lantus composed of hexamer of insulin glargine having substitution and insertion in the B chain of insulin, indicating that the hexamer has a larger volume and stability than the commercial insulin, after subcutaneous injection (Example 7). These results support that the non-peptidyl polymer-insulin multimer of the present invention has excellent in-vivo duration of efficacy and stability, and thus the multimer or a composition including the multimer can be used for the treatment of diabetes.

In another aspect, the present invention provides a preparation method of the non-peptidyl polymer-insulin multimer of the present invention, comprising the step of reacting the non-peptidyl polymer-insulin conjugates with a solution containing cobalt ions to produce non-peptidyl polymer-insulin multimers.

In the present invention, the non-peptidyl polymer-insulin conjugates prepared are reacted with a solution containing cobalt ions so as to prepare the non-peptidyl polymer-insulin multimer according to the present invention, in which the non-peptidyl polymer-insulin conjugate can be prepared by covalently linking insulin with the non-peptidyl polymer having a reactive group selected from aldehyde, maleimide and succinimide derivatives, and isolating the non-peptidyl polymer-insulin conjugates from the reaction mixture.

The succinimide derivative among the reactive groups of the non-peptidyl polymer may be succinimidyl propionate, hydroxy succinimidyl, succinimidyl carboxymethyl, or succinimidyl carbonate.

A molar ratio of the cobalt ion to the non-peptidyl polymer-insulin conjugate may be 0.1 to 1.

Any solution can be used without limitation, as long as the solution contains cobalt ions. Preferably, the solution may contain a salt that dissociates into divalent cobalt ions by solvation in an aqueous solution, a hydrate thereof, a salt that dissociates into divalent cobalt ions by solvation in an aqueous solution and an oxidant, a hydrate of the salt that dissociates into divalent cobalt ions by solvation in an aqueous solution and an oxidant, or a salt that dissociates into trivalent cobalt ions by solvation in an aqueous solution or a hydrate thereof. More preferably, the solution may contain a salt that dissociates into divalent cobalt ions by solvation in an aqueous solution and an oxidant, a hydrate of the salt that dissociates into divalent cobalt ions by solvation in an aqueous solution and an oxidant, or a salt that dissociates into trivalent cobalt ions by solvation in an aqueous solution or a hydrate thereof.

The salt that dissociates into divalent cobalt ions may be cobalt chloride (II) ($CoCl_2$), and the salt that dissociates into trivalent cobalt ions may be cobalt chloride (III) ($CoCl_3$).

In addition, the oxidant useful in the present invention may include a substance such as hydrogen peroxide, which has an oxidizing power to convert the divalent cobalt ions in the aqueous solution and in the non-peptidyl polymer-insulin multimer into trivalent cobalt ions. Preferably, a molar ratio of the oxidant to the divalent cobalt ion may be 0.5 to 5.

Preferably, the reaction may be performed in a buffer solution at pH 5 to 9, and more preferably, in a buffer solution at pH 7.5 to 8.5.

In still another aspect, the present invention provides a pharmaceutical composition for the prevention or treatment of diabetes, comprising the non-peptidyl polymer-insulin multimer of the present invention as an active ingredient.

Further, in still another aspect, the present invention provides a method for preventing or treating diabetes, comprising the step of administering the pharmaceutical composition of the present invention to a subject having diabetes or suspected of having diabetes.

As used herein, the term "diabetes" means a metabolic disease caused by an abnormality in the secretion or function of insulin. The composition of the present invention is administered to a subject so as to control the blood glucose level, thereby treating diabetes.

As used herein, the term "prevention" means all of the actions in which the symptoms of diabetes are restrained or the occurrence of diabetes is retarded by administration of the composition, and the term "treatment" means all of the actions in which the symptoms of diabetes have taken a turn for the better or been modified favorably by administration of the composition. The treatment of diabetes can be applied to any mammal that may have diabetes, and examples thereof include humans and primates as well as livestock such as cattle, pig, sheep, horse, dog, and cat without limitation, and is preferably human.

As used herein, the term "administration" means introduction of a predetermined amount of a substance into a patient by a certain suitable method. The non-peptidyl polymer-insulin multimer may be administered via any of the common routes, as long as it is able to reach a desired tissue. A variety of modes of administration are contemplated, including intraperitoneally, intravenously, intramuscularly, subcutaneously, intradermally, orally, topically, intranasally, intrapulmonarily and intrarectally, but the present invention is not limited to these exemplified modes of administration. However, since peptides are digested upon oral administration, active ingredients of a composition for oral administration should be coated or formulated for protection against degradation in the stomach. Preferably, the multimer may be administered in an injectable form. In addition, the pharmaceutical composition may be administered using a certain apparatus capable of transporting the active ingredients into a target cell.

Figure 4:
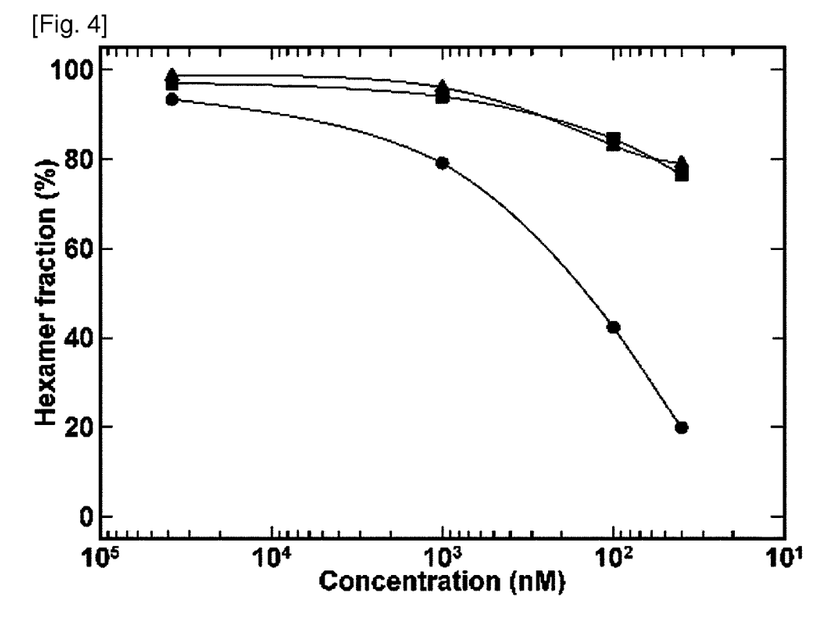
FIG. 4 shows the result of size exclusion chromatography of cobalt PEG (5K)-insulin hexamer (▲), cobalt PEG (20 k)-insulin hexamer (■), and cobalt insulin hexamer (●) purified to examine their dissociation into monomers by Dulbecoo's Phosphate-Buffered Saline (DPBS) dilution.

The non-peptidyl polymer-insulin multimer of the present invention maintains its form without dissociation into monomers in a low concentration range, thereby showing an excellent storability as a pharmaceutical composition (FIG. 4). Therefore, the pharmaceutical composition of the present invention may include the non-peptidyl polymer-insulin multimer of the present invention at a concentration of 0.01 µM to 100 µM, preferably 0.1 µM to 100 µM, more preferably 1 µM to 100 µM, and much more preferably 10 µM to 100 µM.

The pharmaceutical composition of the present invention may include a pharmaceutically acceptable carrier. For oral administration, the pharmaceutically acceptable carrier may include a binder, a lubricant, a disintegrant, an excipient, a solubilizer, a dispersing agent, a stabilizer, a suspending agent, a coloring agent, and a flavor. For injectable preparations, the pharmaceutically acceptable carrier may include a buffering agent, a preserving agent, an analgesic, a solubilizer, an isotonic agent, and a stabilizer. For preparations for topical administration, the pharmaceutically acceptable carrier may include a base, an excipient, a lubricant, and a preserving agent. The pharmaceutical composition of the present invention may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable preparations, the pharmaceutical composition may be formulated into a unit dosage form, such as a multidose container or an ampule as a single-dose dosage form. The pharmaceutical composition may be also formulated into solutions, suspensions, tablets, pills, capsules and long-acting preparations.

On the other hand, examples of the carrier, the excipient, and the diluent suitable for the pharmaceutical formulations include lactose, dextrose, sucrose, sorbitol, mannitol, xylitol, erythritol, maltitol, starch, acacia rubber, alginate, gelatin, calciumphosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical formulations may further include fillers, anti-coagulating agents, lubricants, humectants, flavors, and antiseptics.

The composition of the present invention may be administered in a pharmaceutically effective amount. As used herein, the term "pharmaceutically effective amount" refers to an amount sufficient for the treatment of diseases, which is commensurate with a reasonable benefit/risk ratio applicable for medical treatment. An effective dosage of the present composition may be determined depending on the subject and severity of the disease, age, gender, drug activity, drug sensitivity, administration time, administration routes, excretion rates, duration of treatment, simultaneously used drugs, and other factors known in medicine.

The non-peptidyl polymer-insulin multimer according to the present invention has more excellent in-vivo duration of efficacy and stability than the non-peptidyl polymer-insulin conjugate and the insulin multimer, thereby being useful for the prevention and treatment of diabetes. Thus, administration of the pharmaceutical composition including the same promotes the prevention and treatment of the disease.

In still another aspect, the present invention provides a kit for the preparation of the non-peptidyl polymer-insulin multimer of the present invention, comprising non-peptidyl polymer-insulin conjugates prepared by linking a non-peptidyl polymer and insulin via a covalent bond; and a solution containing cobalt ions, in which the solution contains a salt that dissociates into divalent cobalt ions by solvation in an aqueous solution and an oxidant; a hydrate of the salt that dissociates into divalent cobalt ions by solvation in an aqueous solution and an oxidant; or a salt that dissociates into trivalent cobalt ions by solvation in an aqueous solution or a hydrate thereof.

In the kit for the preparation of the non-peptidyl polymer-insulin multimer of the present invention, the salt or hydrate thereof and the oxidant may be stored in a single container or separately in individual containers.

Further, the kit of the present invention may further include instructions that describe optimal reaction conditions, and a pharmaceutically acceptable carrier. The instructions may include a guidebook such as a pamphlet or brochure, a label attached on the kit, and a description on the surface of a package containing the kit. In addition, the guidebook may include information published or provided through electronic media such as the internet.

[Mode For Invention]

Hereinafter, the present invention will be described in more detail with reference to the following Examples. However, these Examples are for illustrative purposes only, and the invention is not intended to be limited by these Examples.

Example 1

Synthesis and Isolation of PEG-Insulin Conjugate

Figure 1:
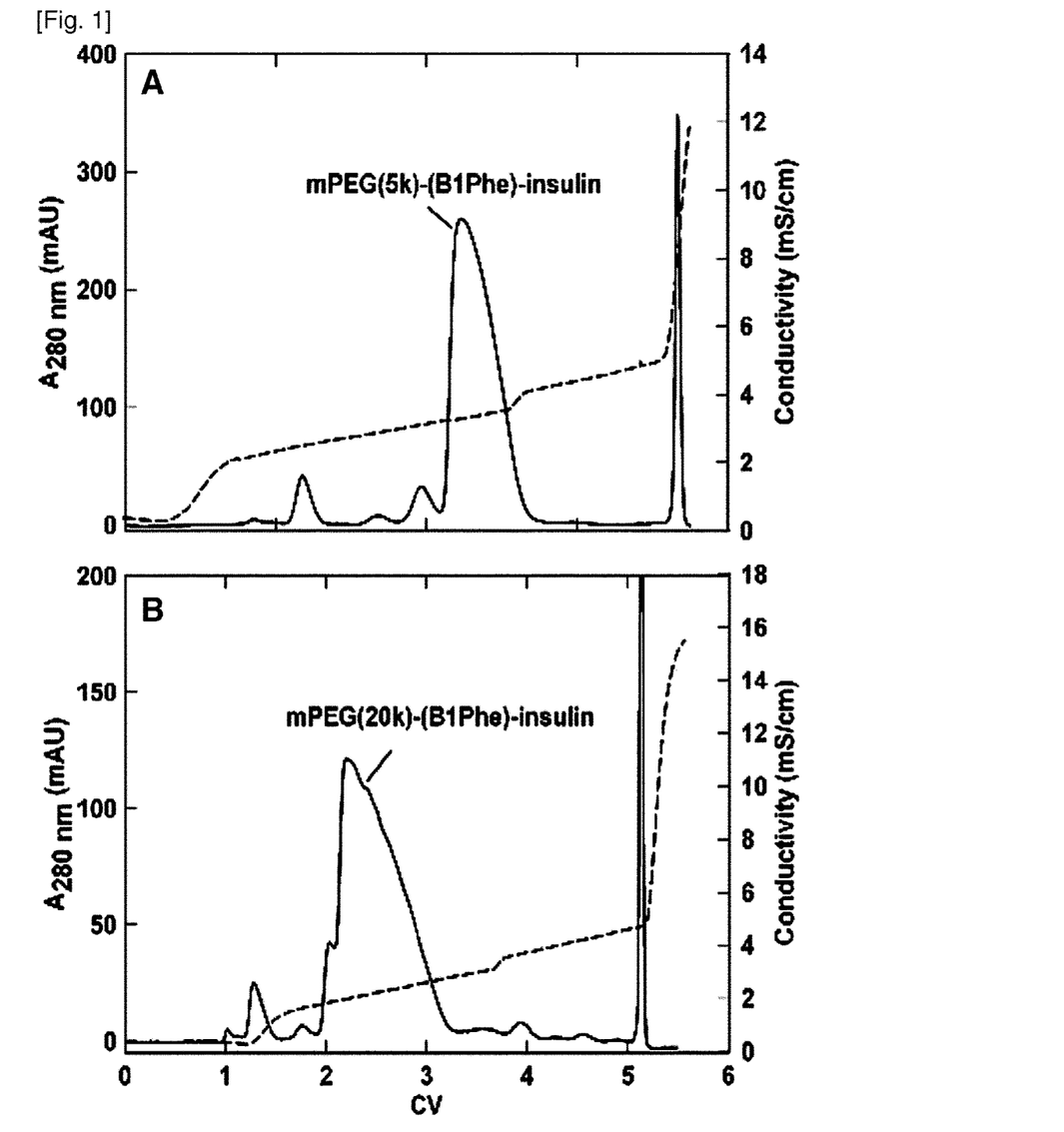
FIG. 1(A) shows the result of cation exchange chromatography (CEC) for isolating insulin where PEG (5 k) is linked to the amino terminus of its B chain.
FIG. 1(B) shows the result of cation exchange chromatography for isolating insulin where PEG (20 k) is linked to the amino terminus of its B chain.

In order to link mPEG-aldehyde (monomethoxypolyethylene glycol-aldehyde) having a molecular weight of 5 k or 20 k to the amino terminus of the B chain of human native insulin, insulin and mPEG-aldehyde were reacted at a molar ratio of 1:2 with the insulin concentration of 2 mg/mL at 4° C. for 12 h. At this time, the reaction was conducted in a 100 mM sodium citrate buffer solution at pH 6.0, and 20 mM sodium cyanoborohydride (SCB) was added thereto as a reducing agent. The insulin mono-PEGylated at the amino terminus of the B chain was isolated from the reaction mixture using a SOURCE 15S (GE Healthcare) resin packed to an HR column (GE Healthcare). As shown in FIG. 1, PEG (5 k or 20 k)-insulin conjugate was observed at the main peak (FIG. 1).

Column: Source 15S medium packed in HR column (GE Healthcare)
Flow rate: 1.8 mL/min
Gradient: A 0→50% 100 min B (A: 20 mM sodium citrate (sodium citrate) pH 3.0+60% ethanol, B: A+0.5M KCl)

Example 2

Peptide Mapping of PEG-Insulin Conjugate

Figure 2:
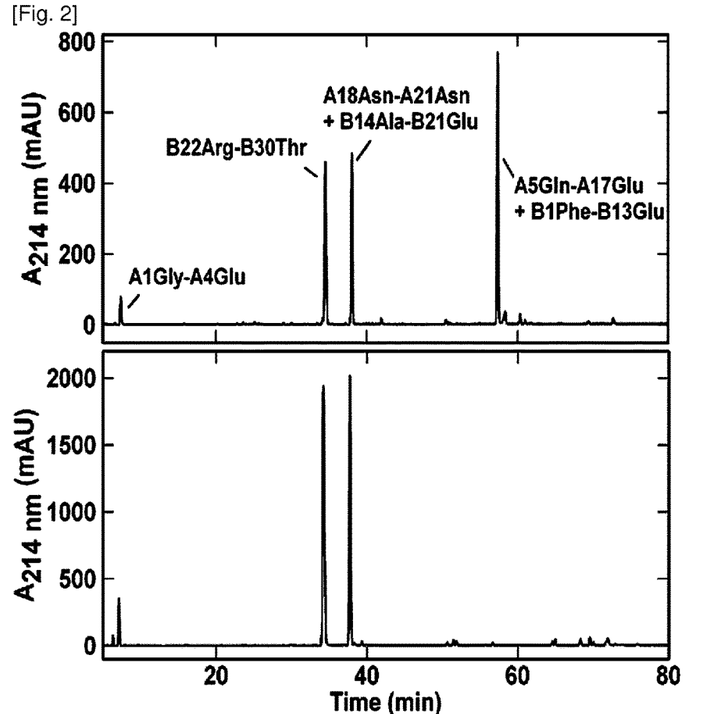
FIG. 2 shows the result of examining the PEG attachment site by comparing the chromatograms of human native insulin fragments (upper) and PEG-insulin conjugate (lower) by Glu-C peptide mapping.

PEG-insulin conjugate or human native insulin was cleaved using Glu-C (Roche Applied Science). The reaction was performed under the conditions of 20 mM HEPES buffer at pH 8.2 and 25° C. for 12 h. The reactant was analyzed by reversed phase high performance liquid chromatography. A Jupiter 5 micron C18 column (Phenomenex, Inc.) was operated on an Agilent 1200 Series module. As shown in FIG. 2, it was found that most of the PEG was linked to the amino terminus of the B chain of insulin (FIG. 2).

Column: Jupiter 5 micron C18 (Phenomenex, Inc.)
Flow rate: 1 mL/min
Gradient: A10→30% 65 min B, A 30→40% 5 min B (A: 20 mM sodium sulfate pH 2.0, B: A+100% acetonitrile)

Example 3

In Vitro Efficacy Test

In order to differentiate murine fibroblast 3T3-L1 into adipocyte, the cell was inoculated in a 48-well plate containing a 10% FBS/DMEM media containing dexamethasone, IBMX, and insulin at a cell density of $1.0 \times 10^5$ per well. The differentiated cells were washed with DPBS three times, and cultured in a serum-free DMEM for 4 h. Human native insulin, PEG (5 k)-insulin, and PEG (20 k)-insulin were prepared in sugar-containing DMEM within a proper concentration range, and then added to the 48-well plate containing the differentiated adipocytes. After cultivation at 37° C. for 24 h, the residual sugar concentration in the media was measured using a D-Glucose assay kit (Megazyme), and $EC_{50}$ values were calculated and shown in Table 1.

TABLE 1

| Protein | $EC_{50}$ (nM) | Relative activity (%) |
| --- | --- | --- |
| Human native insulin | 5.69 ± 1.13 | 100 |
| PEG (5k)-insulin | 9.48 ± 2.77 | 60 |
| PEG (20k)-insulin | 13.55 ± 0.71 | 42 |

These results indicate that PEG-insulin has an insulin activity.

Example 4

Preparation and Purification of Cobalt PEG-Insulin Hexamer

PEG-insulin conjugates in 20 mM HEPES buffer (pH 8.2) were mixed with a cobalt chloride solution to a ratio of cobalt to hexamer of 3:1. To convert divalent cobalt ions into trivalent cobalt ions, hydrogen peroxide corresponding to twice of the total divalent cobalt ions was added, and left at room temperature for 2 h. Thereafter, cobalt PEG-insulin hexamers were isolated by SEC (size exclusion chromatography).

Column: Superdex 200 16/60 prep grade (GE Healthcare)
Flow rate: 0.4 mL/min
Buffer: 20 mM HEPES pH 8.2+0.2 M NaCl

Example 5

Measurement of Hydrodynamic Volume of Cobalt PEG-Insulin Hexamer

Hydrodynamic volume of the PEG-insulin conjugate or the cobalt PEG-insulin hexamer was measured according to the conditions described in Example 4, except that Superdex 200 10/300 GL was used as a column. The regression line was calculated from the elution volume of standard protein. Partition coefficient (Kav) is defined as follows.

$$Kav=(Ve-V0)/(Vt-V0)$$

Ve represents the elution volume, V0 represents the void volume determined by Blue dextran, and Vt represents the bed volume.

Figure 3:
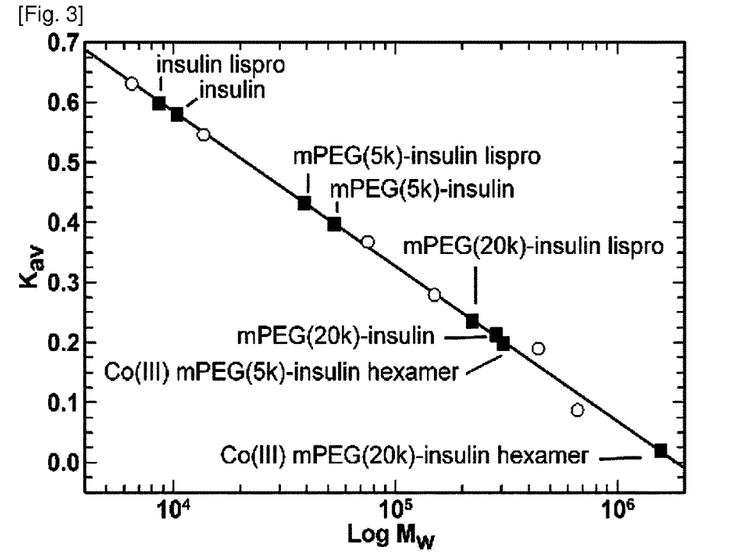
FIG. 3 shows the result of measuring hydrodynamic volumes of PEG-insulin conjugate and cobalt PEG-insulin hexamer by size exclusion chromatography (SEC), in which the regression line was calculated from the elution time of standard proteins (each of the six white circles from the left upper, aprotinin, 6.5 kDa; ribonuclease, 13.7 kDa; conalbumin, 75 kDa; immunoglobulin G, 150 kDa; ferritin, 443 kDa; thyroglobulin, 669 kDa)

As shown in FIG. 3, it was found that the cobalt PEG (5 k)-insulin hexamer (300 kDa) had a hydrodynamic volume approximately 5 times larger than monomer (60 kDa), and the cobalt PEG (20 k)-insulin hexamer (1,600 kDa) had a hydrodynamic volume approximately 10 times larger than monomer (FIG. 3).

These results indicate that the cobalt PEG-insulin multimer has a remarkably large hydrodynamic volume compared to monomers, and thus renal clearance threshold is lowered to increase in-vivo duration of efficacy.

Example 6

Dissociation Measurement of Cobalt PEG-Insulin Hexamer by Dilution

The cobalt PEG-insulin hexamer and the cobalt insulin hexamer purified at a concentration of 100 μM were diluted with DPBS to 1 μM, 0.1 μM, and 0.04 μM. They were left at room temperature for 16 h, and then concentrated to 0.3 mM using a centrifugal concentrator (Vivaspin 20, Sartorius). Analysis was performed according to the conditions described in Example 5. The ratio of hexamer to monomer was calculated from the peak area. As shown in FIG. 4, as the concentration of cobalt insulin hexamer (black circle) decreased, its dissociation into monomers rapidly occurred, and thus the hexamer ratio was decreased to 20% at the concentration of 0.04 μM. However, the ratios of the cobalt PEG (5 k)-insulin hexamer (black triangle) and the cobalt PEG (20 k)-insulin hexamer (black square) were maintained at 70% or higher at the same concentration (FIG. 4).

These results indicate that the cobalt PEG-insulin hexamer exists in a hexamer form with stability even at a low concentration and has a property of slow dissociation into monomers compared to the cobalt insulin hexamer, and thus can be used for the development of long-acting insulin hexamer formulations.

Example 7

Comparison of Molecular Size Between Commercial Long-Acting Insulin and Cobalt PEG-Insulin Hexamer by Size Exclusion Chromatography Size exclusion chromatography was performed to indirectly predict the molecular size of subcutaneously injected insulin formulation and its size change according to natural dilution (Havelund et al., 2004). The representative commercial long-acting insulin formulations, Levemir and Lantus, were used as a control group to examine the relative molecular size of the cobalt PEG-insulin hexamer. Chromatography was performed according to the conditions described in Example 4, except that DPBS was used as a buffer solution to create subcutaneous environment.

As shown in Table 2, the cobalt PEG-insulin hexamer showed shorter elution time and lower dissociation coefficient than Levemir and Lantus. These results suggest that the cobalt PEG-insulin hexamer will maintain its large volume and stable hexamer form after subcutaneous injection, compared to the two commercially available long-acting insulin formulations (Table 2).

TABLE 2

| Protein | Elution time (min) | Dissociation coefficient ($K_{av}$) |
|---|---|---|
| Levemir | 47.56 | 0.69 |
| Lantus | 46.82 | 0.67 |
| Cobalt PEG (5k)-insulin hexamer | 27.63 | 0.20 |
| Cobalt PEG (20k)-insulin hexamer | 20.12 | 0.01 |

---

The invention claimed is:

1. A non-peptidyl polymer-insulin multimer, consisting essentially of two or more non-peptidyl polymer-insulin conjugates, each of said non-peptidyl polymer-insulin conjugates comprising a non-peptidyl polymer and a native insulin comprising a B chain,
wherein the non-peptidyl polymer and the native insulin are linked to each other via a covalent bond,
wherein the insulin part of the conjugates is complexed with a trivalent cobalt ion to form a multimer,
wherein the non-peptidyl polymer has an aldehyde reactive group and is linked to the amino terminus of the B chain of insulin, via a covalent bond formed by the aldehyde reactive group, and
wherein the non-peptidyl polymer is polyethylene glycol.

2. The multimer according to claim 1, wherein the polyethylene glycol has a molecular weight of 5 to 100 kDa.

3. The multimer according to claim 1, wherein the non-peptidyl polymer covalently bound to the native insulin has a reactive group of propion aldehyde, or butyl aldehyde.

4. The multimer according to claim 1, wherein the non-peptidyl polymer-insulin multimer is a non-peptidyl polymer-insulin hexamer.

5. A pharmaceutical composition, comprising the non-peptidyl polymer-insulin multimer of any one of claims 1, 2, 3, and 4 as an active ingredient and a pharmaceutically acceptable carrier.

6. The composition of claim 5, comprising the non-peptidyl polymer-insulin multimer at a concentration of 0.01 μM to 100 μM.

7. A kit for the preparation of the non-peptidyl polymer-insulin multimer of any one of claims 1, 2, 3, and 4, comprising
(a) non-peptidyl polymer-insulin conjugates comprising a non-peptidyl polymer and a native insulin comprising a B chain, wherein the non-peptidyl polymer and the native insulin are linked to each other via a covalent bond; and
(b) a solution containing trivalent cobalt ions,
wherein the solution contains a salt that dissociates into trivalent cobalt ions by solvation in an aqueous solution or a hydrate thereof,
wherein the non-peptidyl polymer has an aldehyde reactive group and is linked to the amino terminus of the B chain of insulin, via a covalent bond formed by the aldehyde reactive group, and wherein the non-peptidyl polymer is polyethylene glycol.

8. The kit according to claim 7, wherein the salt or the hydrate thereof are separately in individual containers.

9. The kit according to claim 7, wherein the aldehyde reactive group is propion-aldehyde or butyl aldehyde.

10. A method for treating diabetes, comprising the step of administering the pharmaceutical composition of claim 5 to a subject having diabetes.

11. A preparation method of the non-peptidyl polymer-insulin multimer of claim 1, comprising the step of reacting non-peptidyl polymer-insulin conjugates with a solution containing trivalent cobalt ions to produce non-peptidyl polymer-insulin multimers,
wherein the non-peptidyl polymer-insulin conjugates comprises a non-peptidyl polymer and a native insulin comprising a B chain,
wherein the non-peptidyl polymer has an aldehyde reactive group and is linked to the amino terminus of the B chain of insulin, via a covalent bond formed by the aldehyde reactive group, and
wherein the non-peptidyl polymer is polyethylene glycol.

12. The preparation method according to claim 11, wherein the solution contains a salt that dissociates into trivalent cobalt ions by solvation in an aqueous solution, or a hydrate of the salt.

13. The preparation method according to claim 12, wherein the salt that dissociates into trivalent cobalt ions is cobalt chloride (III) ($CoCl_3$).

14. The preparation method according to claim 11, wherein a molar ratio of the trivalent cobalt ions to the non-peptidyl polymer-insulin conjugate is 0.1 to 1.

15. The preparation method according to claim 11, wherein the reaction is performed in a buffer solution at pH 5 to 9.

16. The preparation method according to claim 11, wherein the reactive group is propion-aldehyde or butyl aldehyde.

* * * * *

SEQUENCE LISTING

<160> NUMBER OF SEQ ID NOS: 2

<210> SEQ ID NO 1
<211> LENGTH: 21
<212> TYPE: PRT
<213> ORGANISM: Artificial Sequence
<220> FEATURE:
<223> OTHER INFORMATION: A chain of insulin

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Artificial Sequence
<220> FEATURE:
<223> OTHER INFORMATION: B chain of insulin

```
<400> SEQUENCE: 2

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Thr
            20                  25                  30
```